(12) United States Patent
Yamashita et al.

(10) Patent No.: US 10,835,643 B2
(45) Date of Patent: *Nov. 17, 2020

(54) DRUG COATING LAYER

(71) Applicant: Terumo Kabushiki Kaisha, Tokyo (JP)

(72) Inventors: Keiko Yamashita, Kanagawa (JP); Hiroshi Goto, Kanagawa (JP); Shigenori Nozawa, Kanagawa (JP); Katsumi Morimoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/869,822

(22) Filed: Jan. 12, 2018

(65) Prior Publication Data

US 2018/0154049 A1  Jun. 7, 2018

Related U.S. Application Data

(63) Continuation of application No. 14/228,659, filed on Mar. 28, 2014, now Pat. No. 9,872,940.

(30) Foreign Application Priority Data

Apr. 1, 2013 (JP) .................. 2013-076434

(51) Int. Cl.
A61L 31/08 (2006.01)
A61L 29/08 (2006.01)
(Continued)

(52) U.S. Cl.
CPC ............ A61L 29/08 (2013.01); A61L 29/16 (2013.01); A61L 31/08 (2013.01); A61L 31/16 (2013.01);
(Continued)

(58) Field of Classification Search
None
See application file for complete search history.

(56) References Cited

U.S. PATENT DOCUMENTS 6,558,405 B1  5/2003  McInnes
8,597,720 B2  12/2013  Hoffman et al.
(Continued)

FOREIGN PATENT DOCUMENTS

AU  2014250424 B2  10/2014
CN  101854962 A   10/2010
(Continued)

OTHER PUBLICATIONS

Office Actioin issued by the Australian Patent Office in corresponding Australian Patent Application No. 2014250424 dated Dec. 8, 2015 (3 pages).
(Continued)

*Primary Examiner* — Susan T Tran
(74) *Attorney, Agent, or Firm* — Buchanan Ingersoll & Rooney PC

(57) ABSTRACT

A drug coating layer on a non-porous nylon elastomer balloon substrate surface comprising a plurality of elongated bodies with long axes wherein each elongated body is formed of a crystal of a water-insoluble drug and is independently formed on the substrate surface, wherein the long axes of the elongated bodies are substantially linear in shape, and the long axes of the elongated bodies form an angle in a predetermined range with respect to a substrate plane with which the long axis of the elongated body intersects. The drug coating layer can provide low toxicity and a high intravascular stenosis inhibitory effect.

4 Claims, 7 Drawing Sheets

(51) Int. Cl.
*A61L 31/16* (2006.01)
*A61M 25/10* (2013.01)
*A61L 29/16* (2006.01)
*A61K 9/00* (2006.01)

(52) U.S. Cl.
CPC .......... *A61M 25/10* (2013.01); *A61M 25/104* (2013.01); *A61K 9/0004* (2013.01); *A61L 2300/416* (2013.01); *A61L 2300/63* (2013.01); *A61M 2025/105* (2013.01)

(56) References Cited

U.S. PATENT DOCUMENTS

| | | | |
|---|---|---|---|
| 2003/0144344 | A1 | 7/2003 | Benigni et al. |
| 2008/0097301 | A1 | 4/2008 | Alpini et al. |
| 2008/0097374 | A1 | 4/2008 | Korleski et al. |
| 2008/0118544 | A1 | 5/2008 | Wang |
| 2009/0093870 | A1 | 4/2009 | Menendez et al. |
| 2009/0246252 | A1 | 10/2009 | Arps et al. |
| 2010/0034960 | A1 | 2/2010 | Kindaichi et al. |
| 2010/0040766 | A1 | 2/2010 | Chappa et al. |
| 2010/0049296 | A1 | 2/2010 | Sarasam et al. |
| 2010/0055294 | A1 | 3/2010 | Wang et al. |
| 2010/0104734 | A1 | 4/2010 | Orosa et al. |
| 2010/0209472 | A1 | 8/2010 | Wang |
| 2010/0272773 | A1 | 10/2010 | Kangas et al. |
| 2011/0015664 | A1 | 1/2011 | Kangas et al. |
| 2011/0022027 | A1* | 1/2011 | Morishita .............. A61L 29/085 604/509 |
| 2011/0034994 | A1 | 2/2011 | Lewis et al. |
| 2011/0238011 | A1 | 9/2011 | Scheller et al. |
| 2011/0281020 | A1 | 11/2011 | Gong et al. |
| 2011/0295200 | A1 | 12/2011 | Speck et al. |
| 2012/0015019 | A1 | 1/2012 | Pacetti et al. |
| 2012/0100279 | A1 | 4/2012 | Neumann et al. |
| 2012/0128863 | A1 | 5/2012 | Nguyen et al. |
| 2013/0142834 | A1 | 6/2013 | Esfand et al. |
| 2013/0337147 | A1 | 12/2013 | Chappa et al. |
| 2014/0271775 | A1* | 9/2014 | Cleek ...................... A61L 27/16 424/423 |
| 2014/0328998 | A1 | 11/2014 | Chappa et al. |
| 2014/0358122 | A1 | 12/2014 | Yamashita et al. |
| 2015/0328369 | A1 | 11/2015 | Yamashita et al. |
| 2015/0328371 | A1 | 11/2015 | Yamashita et al. |
| 2015/0328372 | A1 | 11/2015 | Yamashita et al. |
| 2016/0015861 | A1 | 1/2016 | Yamashita et al. |
| 2016/0310709 | A1 | 10/2016 | Gotou et al. |
| 2017/0014601 | A1 | 1/2017 | Kurosaki et al. |
| 2017/0014603 | A1 | 1/2017 | Kurosaki et al. |
| 2017/0014860 | A1 | 1/2017 | Kurosaki et al. |
| 2017/0021142 | A1 | 1/2017 | Kurosaki et al. |

FOREIGN PATENT DOCUMENTS

| | | | |
|---|---|---|---|
| EP | 0 128 859 | A1 | 12/1984 |
| EP | 168818 | B1 * | 12/2011 .............. A61L 27/34 |
| EP | 1684818 | B1 | 12/2011 |
| EP | 2 944 334 | A1 | 11/2015 |
| JP | 59-207854 | A | 11/1984 |
| JP | 2005-59225 | A | 3/2005 |
| JP | 2010-509991 | A | 4/2010 |
| JP | 2010-535074 | A | 11/2010 |
| JP | 2010-540159 | A | 12/2010 |
| JP | 2012-514510 | A | 6/2012 |
| JP | 2012-533338 | A | 12/2012 |
| JP | 2013-514278 | A | 4/2013 |
| WO | WO-2004006976 | A1 * | 1/2004 .............. A61F 2/958 |
| WO | 2005/051445 | A1 | 6/2005 |
| WO | WO 2008/063576 | A2 | 5/2008 |
| WO | WO 2008/063581 | A2 | 5/2008 |
| WO | 2008/131131 | A1 | 10/2008 |
| WO | WO 2009/051614 | A1 | 4/2009 |
| WO | WO 2009/051615 | A1 | 4/2009 |
| WO | WO 2009/051616 | A1 | 4/2009 |
| WO | WO 2009/051618 | A1 | 4/2009 |
| WO | WO 2010/030995 | A2 | 3/2010 |
| WO | WO 2010/079218 | A2 | 7/2010 |
| WO | 2010/086863 | A2 | 8/2010 |
| WO | WO 2010/124098 | A2 | 10/2010 |
| WO | WO 2011/008393 | A2 | 1/2011 |
| WO | WO 2011/119159 | A1 | 9/2011 |
| WO | WO 2013/181498 | A1 | 12/2013 |
| WO | WO 2014/152360 | A1 | 9/2014 |
| WO | WO 2014/163091 | A1 | 10/2014 |

OTHER PUBLICATIONS

Buszman et al., "Tissue Uptake, Distribution, and Healing Response After Delivery of Paclitaxal via Second-Generation Iopromide-Based Balloon Coating", JACC: Cardiovascular Interventions, The American College of Cardiology Foundation, (Aug. 2013), vol. 6, No. 8, pp. 883-890.

Gyoengyoesi et al. "TCT-807 Optical Coherence Tomography, Physiologic Vascular Function, Safety and Efficacy Preclinical Studies of Porcine Peripheral Vessels Dilated with Drug-Coated Balloon", (Oct. 29, 2013), JACC vol. 62/18/Suppl B, pp. B245.

Joner et al., "Comparative assessment of drug-eluting balloons in an advanced porcine model of coronary restenosis", Thrombosis and Haemostasis, (May 2011), vol. 105, No. 5, pp. 864-872.

Melder et al., "IN.PACT DEB Technology and Pre-clinical Science", Leipzig Interventional Course (LINC), 2013 (month unknown), pp. 1-18.

Ranger™, "Paclitaxel-Coated PTA Balloon Catheter", Boston Scientific, retrieved on May 16, 2014, pp. 1-6.

Schmidt et al., "First Experience With Drug-Eluting Balloons in Infrapopliteal Arteries", Journal of the American College of Cardiology, (Sep. 2011), vol. 58, No. 11, pp. 1105-1109.

Virmani, "Pre-clinical safety data and technology review", Leipzig Interventional Course (LINC), CVPath Institute, Gaithersburg, Maryland, www.cvpath.org, 2014 (month unknown), pp. 1-22.

Virmani, "Pros and Cons of Different Technologies in Peripheral Arteries: Insights from a Pathologist", CVPath Institute Inc., Gaithersburg, Maryland, pp. 1-41.

Von Strandmann, "Effect of drug-coated balloon on porcine peripheral arteries: physiologic vascular function, safety and efficacy experiments", Euro PCR, 2013 (month unknown), pp. 1-20.

Yazdani et al., "Vascular, Downstream, and Pharmacokinetic Responses to Treatment with a Low Dose Drug-Coated Balloon in a Swine Femoral Artery Model", Catherization and Cardiovascular Interventions, Jan. 2014, vol. 83, No. 1, pp. 132-140.

International Search Report (Form PCT/ISA/210) dated Jun. 17, 2014, by the Japanese Patent Office in International Application No. PCT/JP2014/059665. (5 pages).

Extended Search Report issued by the European Patent Office in European Patent Application No. 14779028.1 dated Jan. 25, 2017 (11 pages).

Office Action issued by the Canadian Intellectual Property Office in Canadian Patent Application No. 2,908,420 dated Jan. 26, 2017 (4 pages).

Extended Search Report issued by the European Patent Office in European Patent Application No. 15709082.0 dated Mar. 8, 2017 (7 pages).

Extended Search Report issued by the European Patent Office in European Patent Application No. 15709083.8 dated Mar. 8, 2017 (8 pages).

Extended Search Report issued by the European Patent Office in European Patent Application No. 15709081.2 dated Mar. 8, 2017 (6 pages).

International Search Report (PCT/ISA/210) dated Jun. 16, 2015, by the Japanese Patent Office as the International Searching Authority for International Application No. PCT/JP2015/058546 (3 pages).

Written Opinion (PCT/ISA/237) dated Jun. 16, 2015, by the Japanese Patent Office as the International Searching Authority for International Application No. PCT/JP2015/058546 (4 pages).

International Search Report (PCT/ISA/210) dated Jun. 16, 2015, by the Japanese Patent Office as the International Searching Authority for International Application No. PCT/JP2015/058547 (3 pages).

(56) References Cited

OTHER PUBLICATIONS

Written Opinion (PCT/ISA/237) dated Jun. 16, 2015, by the Japanese Patent Office as the International Searching Authority for International Application No. PCT/JP2015/058547 (4 pages).
International Search Report (PCT/ISA/210) dated Aug. 4, 2015, by the Japanese Patent Office as the International Searching Authority for International Application No. PCT/JP2015/058548 (5 pages).
Written Opinion (PCT/ISA/237) dated Aug. 4, 2015, by the Japanese Patent Office as the International Searching Authority for International Application No. PCT/JP2015/058548 (5 pages).
Poletto et al. "Characterization of Polyamide 66 Membranes Prepared by Phase Inversion Using Formic Acid and Hydrochloric Acid Such as Solvents"; May 5, 2011: 14(4):547-551.
Notification of Reasons for Refusal issued by the Japanese Patent Office in corresponding Japanese Patent Application No. 2015-510103 dated Jun. 12, 2018 (16 pages including partial English translation).
Office Action and Search Report dated Jun. 4, 2019, by the Russian Patent Office in corresponding Russian Patent Application No. 2018108574/04(013203) (12 pages including English Translation of Office Action and Search Report).
First Office Action issued by The State Intellectual Property Office of People's Republic of China in corresponding Chinese Patent Application No. 201710508711.3 dated Sep. 30, 2019 (12 pages including partial English translation).
Notice of Reasons for Refusal issued by the Japanese Patent Office in corresponding Japanese Patent Application No. 2018-151866 dated Oct. 1, 2019 (14 pages including English translation).
Search Report issued in Chinese Patent Application No. 2017105087113 dated Sep. 30, 2019 (3 pages).

\* cited by examiner

DRUG COATING LAYER

CROSS-REFERENCE TO RELATED APPLICATIONS

This application is a continuation of U.S. application Ser. No. 14/228,659 filed on Mar. 28, 2014, which claims priority to Japanese Application No. 2013-076434 filed on Apr. 1, 2013, the entire contents of which are incorporated herein by reference.

TECHNICAL FIELD

Disclosed is a drug coating layer of water-insoluble drugs, and a drug coating layer exhibiting a specific crystalline morphological form of the water-insoluble drugs.

BACKGROUND DISCUSSION

In recent years, development of a drug eluting balloon (DEB) in which a balloon catheter is coated with drugs has been actively performed, and it has been reported to be effective in the treatment and prevention of restenosis. The balloon is coated by a coating film including drugs and additives, and when a blood vessel is dilated, the balloon presses against a blood vessel wall, and it delivers the drugs to target tissue.

In recent years, it has been found that a morphological form of the drugs coated on the balloon surface influences releasing property and tissue transferability of drugs from the balloon surface in a lesion affected area, and it is known that control of the crystal form or amorphous form of drugs is important.

International Publication No. WO2010/124098 and JP-T-2012-533338 disclose a method in which by using annealing by solvent vapor, the morphological form of drugs coated on a balloon surface is changed from the amorphous to the crystal form. JP-T-2012-533338 further discloses that the crystal form of paclitaxel obtained by annealing has a fan-like form and a rod-like form or a needle-like form, and the rod-like crystal form has a higher concentration of drugs in the target tissue compared to the fan-like form.

In addition, JP-T-2012-514510 discloses that paclitaxel in a crystalline hydrated form is coated, and the crystalline hydrated form has a preferable releasing property and tissue transferability of drugs in the lesion affected area compared to a non-hydrated form and the amorphous.

Thus, JP-T-2012-514510 discloses that the drug eluting balloon having a crystal form paclitaxel exhibits excellent tissue transferability of drugs; however, it does not describe the detailed morphological form of a crystal and an intravascular stenosis inhibitory effect.

In contrast, there is a concern that the drug eluting balloon having a crystal form paclitaxel exhibits strong toxicity with respect to target tissue in some cases. Therefore, in the recent development of the drug eluting balloon, it is required that the drug eluting balloon have both performance, that is, a high effect (intravascular stenosis inhibitory effect) of drugs and low toxicity. In PCT International Publication No. WO2010/124098, JP-T-2012-533338 and JP-T-2012-514510, the toxicity is not described at all, and a crystalline morphological form of a drug for obtaining performance in which the stenosis inhibitory effect is high and the toxicity is low is not yet clear.

Based on what has been described above, since it cannot be said that the drug eluting balloon having a coating layer in the related art sufficiently exhibits low toxicity and a high effect on a stenosis inhibition rate when treating a stenosis portion in a blood vessel, a medical instrument of which the toxicity is even lower and the stenosis inhibiting effect is high is desired.

SUMMARY

A challenge in the art is to provide a drug coating layer having a morphological form of water-insoluble drugs of which the intravascular stenosis inhibitory effect in a lesion affected area is high, when delivering medical equipment coated with a drug into the body and medical equipment using the same.

The challenge is addressed by a drug coating layer having a specific crystalline morphological form of a water-insoluble drug which has a high intravascular stenosis inhibitory effect in a lesion affected area.

Various aspects are disclosed as follows:

(1) A drug coating layer which has a morphological form including a plurality of elongated bodies with long axes that each crystal of a water-insoluble drug independently has, on a substrate surface, in which the long axes of the elongated bodies are nearly linear in shape, and the long axes of the elongated bodies form an angle in a predetermined range, preferably an angle in a range of 45° to 135°, with respect to a substrate plane with which the long axis of the elongated body intersects.

(2) The drug coating layer described in (1) in which at least near the distal of the elongated body is hollow.

(3) The drug coating layer described in (1) or (2) in which a cross-sectional shape of the elongated body on a surface perpendicular to the long axis is a polygon.

(4) The drug coating layer which is a drug coating layer in which crystals of a flatly elongated hair-like shape of crystals of the water-insoluble drug are randomly laminated on the substrate surface, and in which the long axes of some of the crystals have a portion curved in shape, and crystals having other shapes are not mixed in the same crystal plane.

(5) The drug coating layer described in (4) in which the surface of the crystal of the water-insoluble drug is covered with an amorphous film.

(6) The drug coating layer including a crystalline morphological form of the water-insoluble drug, crystal particles of the water-insoluble drug arranged with regularity on the substrate surface, and excipient particles formed of an excipient irregularly arranged between the crystal particles, wherein a molecular weight of the excipient is less than a molecular weight of the water-insoluble drug, a ratio occupied by the excipient particles per a predetermined area of the substrate is less than a ratio occupied by the crystal particles, and the excipient particles do not form a matrix.

(7) The drug coating layer described in any one of (1) to (6) in which the water-insoluble drug is rapamycin, paclitaxel, docetaxel, or everolimus.

(8) Medical equipment having the drug coating layer described in any one of (1) to (7) on the surface of the medical equipment, which is reduced in diameter to be delivered when delivered into a body, and enlarged in diameter to release a drug from the drug coating layer at an affected part.

(9) A method for delivering a drug having a step of delivering the medical equipment described in (8) to a lumen, a step of radially dilating a dilatable portion provided in the medical equipment, and a step in which the drug coating layer which has the dilatable portion is applied to the lumen.

A drug coating layer for drug eluting medical equipment can be provided of which the intravascular stenosis inhibitory effect in a lesion affected area is high and/or the toxicity is low.

BRIEF DESCRIPTION OF THE DRAWINGS

FIG. 1A is a SEM image at 2,000 times magnification of crystals observed on a substrate surface of the drug coating layer prepared in Example 1. FIG. 1B is a SEM image at 1,000 times magnification of crystals observed on another portion of a substrate surface prepared in Example 1. FIG. 1C is a SEM image at 400 times magnification of crystals observed on another portion of the substrate surface prepared in Example 1. FIG. 1D is a SEM image at 4,000 times magnification of crystals observed at a cross-section perpendicular to the substrate surface of the drug coating layer prepared in Example 1.

DETAILED DESCRIPTION

Figure 1A:
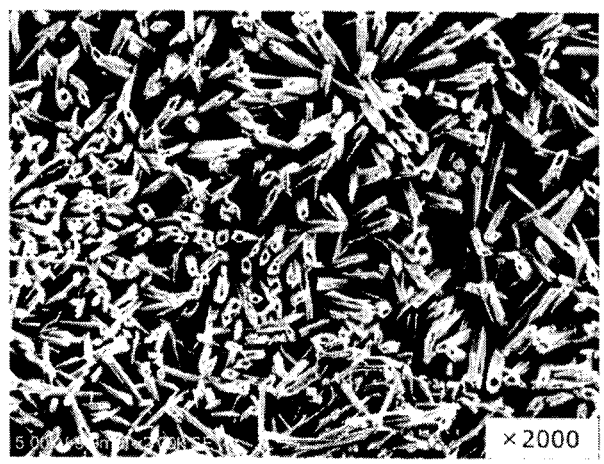
FIGS. 1A-1D are diagrams showing scanning electron microscopic images (hereinafter, referred to as SEM) of a surface of a drug coating layer prepared in Example 1.
Figure 1B:
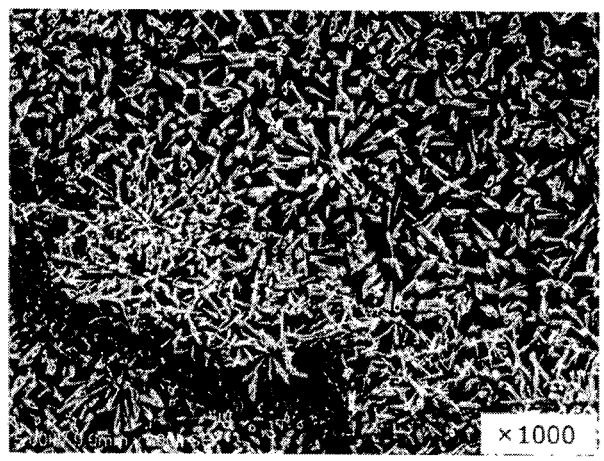
Figure 1C:
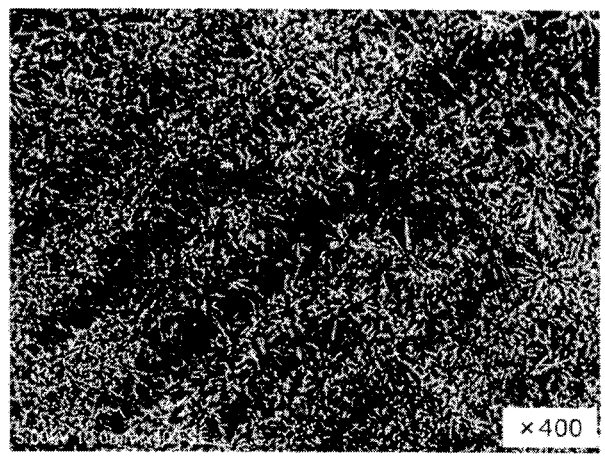
Figure 1D:
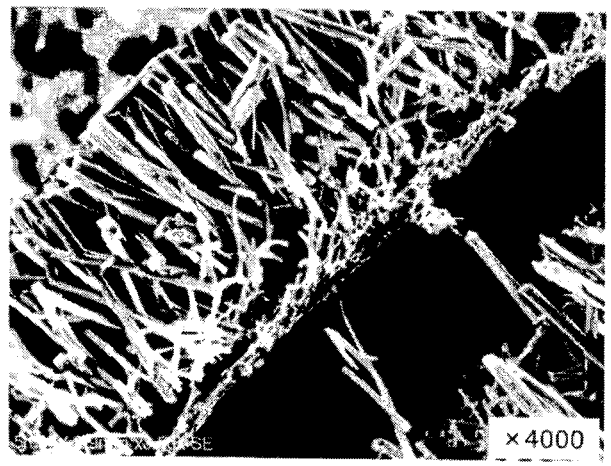
Figure 2:
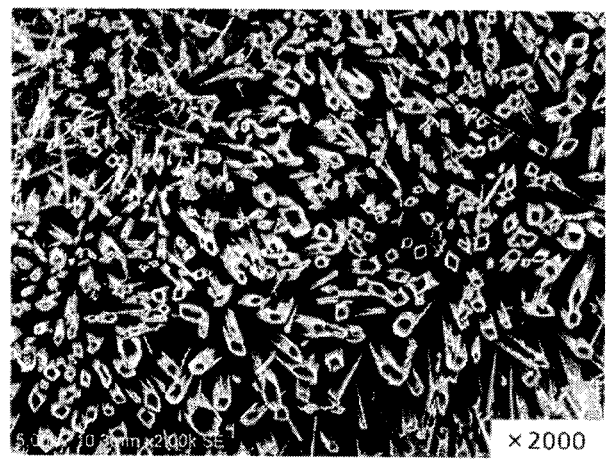
FIG. 2 is a diagram showing a SEM image at 2,000 times magnification of crystals observed on the substrate surface of the drug coating layer prepared in Example 2.
Figure 3A:
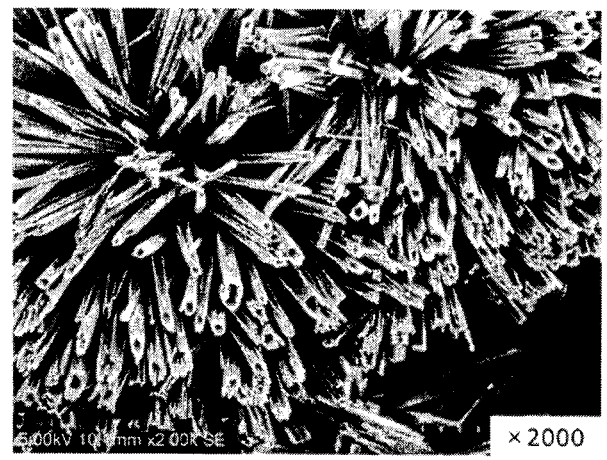
FIG. 3A is a diagram showing a SEM image at 2,000 times magnification of crystals observed on the substrate surface of the drug coating layer prepared in Example 3.
Figure 3B:
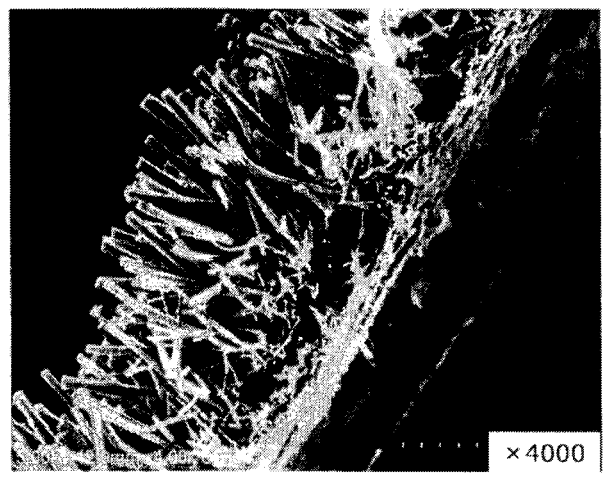
FIG. 3B is a SEM image at 4,000 times magnification of crystals observed at a cross-section perpendicular to the substrate surface of the drug coating layer prepared in Example 3.
Figure 4:
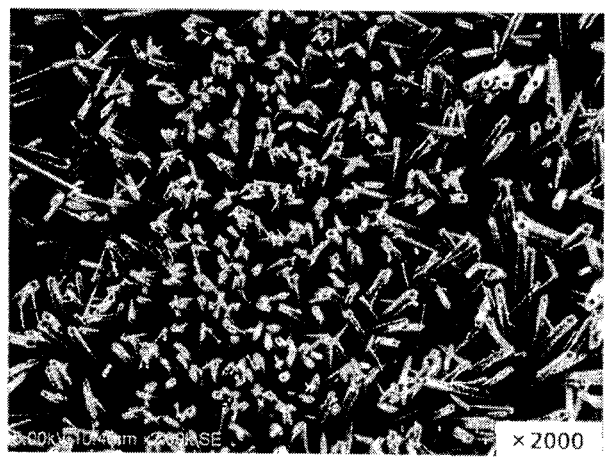
FIG. 4 is a diagram showing a SEM image at 2,000 times magnification of crystals observed on the substrate surface of the drug coating layer prepared in Example 4.
Figure 5:
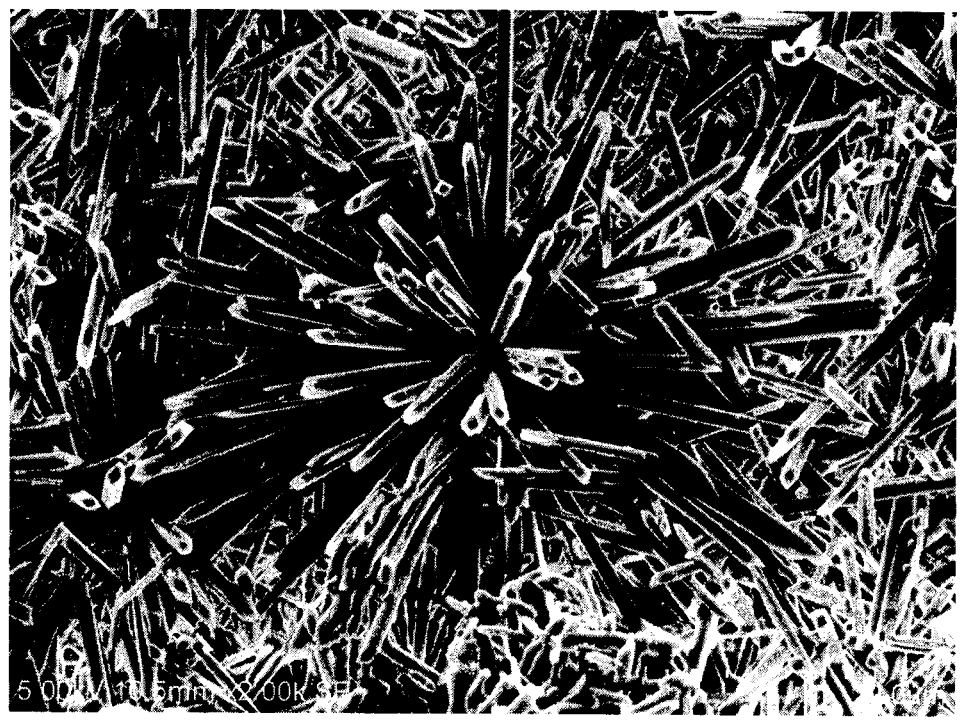
FIG. 5 is a diagram showing a SEM image at 2,000 times magnification of crystals observed on the substrate surface of the drug coating layer prepared in Example 5.

It has been determined that a drug coating layer having low toxicity in the lesion affected area and a high intravascular stenosis inhibitory effect, can be provided with a specific crystal form of a water-insoluble drug when delivering medical equipment coated with a drug into the body.

The following crystal forms are preferably exemplified.

(1) Layer Including Crystalline Morphological Form of Long Hollow Object

The layer having a morphological form including crystals of a long hollow object is a drug coating layer in which a plurality of elongated bodies having long axes formed of crystals of the water-insoluble drug are present in a brush shape on the substrate surface. The plurality of elongated bodies are circumferentially arranged in a brush shape on the substrate surface. Each of the elongated bodies is independently present, has a length, and has one end (proximal) of the elongated body fixed to the substrate surface. The elongated bodies do not form a composite structure with adjacent elongated bodies, and are not connected to each other. The long axis of the crystal is nearly linear in shape. The elongated body forms a predetermined angle with respect to the substrate plane which the long axis intersects. The predetermined angle is in the range of 45° to 135°. The predetermined angle is preferably in the range of 70° to 110°, and more preferably in the range of 80° to 100°. It is more preferable that the long axis of the elongated body forms an angle of nearly 90° with respect to the substrate plane. At least near the distal, the elongated body is hollow. The cross section of the elongated body is hollow in a surface perpendicular to the long axis of the elongated body. The hollow cross section of the elongated body in a surface perpendicular to the long axis is a polygon. Examples of the polygon include a tetragon, a pentagon, and a hexagon. Accordingly, the elongated body has the distal (or distal surface) and the proximal (or proximal surface), and a side surface between the distal (or distal surface) and the proximal (or proximal surface) is formed as a long polyhedron which is constituted with a plurality of planes. The crystalline morphological form constitutes the whole of or at least a part of a plane on the substrate surface. For example, the layer including the crystalline morphological form of the long hollow object is a layer having the crystalline morphological form shown in SEM images of FIGS. 1 to 5.

For example, characteristics of the layer having the morphological form including the crystals of a long hollow object are as follows.

1) A plurality of elongated bodies (rod) having independent long axes, and the elongated body is hollow.

2) The elongated body has a rod shape.

3) The elongated bodies have long axes, and in many cases, is a polyhedron, in which the cross section of the elongated body in a surface perpendicular to the long axis is polygonal. Equal to or greater than 50% by volume of the elongated body crystal is a long polyhedron. The side surface of the polyhedron is mainly a tetrahedron. In some cases, the long polyhedron has a plurality of surfaces (grooves) which are formed of a reentrant angle in which a vertex is extended in a long axis direction. Herein, the reentrant angle means that at least one of the interior angles of the polygon of a cross section of the elongated body in a plane perpendicular to the long axis is greater than an angle of 180°.

4) In many cases, the elongated body having a long axis is a long polyhedron. When viewed in a cross section perpendicular to the long axis, the cross section is polygonal, and is observed as a tetragon, a pentagon, or a hexagon.

5) A plurality of elongated bodies having independent long axes stand in a row with an angle in a predetermined range, preferably in the range of 45° to 135° with respect to the substrate surface, that is, the plurality of elongated bodies having independent long axes nearly uniformly stand like a forest on the substrate surface. The region where the elongated bodies stand like a forest is nearly uniformly formed in the circumferential direction and the axial direction on the substrate surface. Each angle with respect to the substrate surface of each independent elongated body may be different or the same in the predetermined range.

6) One end (proximal) of each elongated body having an independent long axis is fixed to the substrate surface.

7) In some cases, in a portion near the substrate surface, particle-like, short rod-like or short curve-like crystals are laminated. The elongated body which directly or indirectly has a long axis on the substrate surface is present. Therefore, there is a case where the elongated bodies having long axes on the laminate stand like a forest.

8) A length in the axial direction of the elongated body having a long axis is preferably 5 µm to 20 µm, more preferably 9 µm to 11 µm, and still more preferably about 10 µm. A diameter of the elongated body having a long axis is preferably 0.01 µm to 5 µm, more preferably 0.05 µm to 4 µm, and still more preferably 0.1 µm to 3 µm.

9) Other morphological forms (for example, a plate shaped morphological form which is amorphous) are not mixed on the surface of the layer including the crystalline morphological form of a long hollow object, which is present in an amount equal to or greater than 50% by volume, and more preferably equal to or greater than 70% by volume, and is present as the crystalline morphological forms of 1) to 7). More preferably, almost all of the long hollow object is the crystalline morphological form of 7).

10) In the crystalline morphological form of the long hollow object, it is possible that other compounds are present in the drug coating layer including the water-insoluble drug constituting crystals. In this case, the compounds are present in a state of being distributed in the space between crystals (elongated body) of a plurality of the water-insoluble drugs which stand like a forest on a balloon substrate surface. In the ratio of the materials constituting the drug coating layer, the crystals of the water-insoluble drugs occupy a much greater volume than other compounds in this case.

11) In the crystalline morphological form of long hollow object, the water-insoluble drugs constituting crystals are present on the balloon substrate surface. In the drug coating layer of the balloon substrate surface having the water-insoluble drugs constituting crystals, a matrix by the excipient is not formed. Therefore, the water-insoluble drugs constituting crystals are not attached to the matrix material. The water-insoluble drugs constituting crystals are also not embedded in the matrix material.

12) In the crystalline morphological form of long hollow object, the drug coating layer may include crystal particles of the water-insoluble drugs which are arranged with regularity on the substrate surface, and excipient particles formed of an excipient which are irregularly arranged between the crystal particles. In this case, a molecular weight of the excipient is less than a molecular weight of the water-insoluble drugs. Therefore, the ratio that the excipient particles occupy per a predetermined area of the substrate is smaller than the ratio that crystal particles occupy and the excipient particles do not form a matrix. Here, the crystal particles of the water-insoluble drugs may be one of the elongated body, and since the excipient particles are present in a state of being much smaller than the crystal particles of the water-insoluble drugs, and are dispersed among the crystal particles of the water-insoluble drugs, there is a case where the excipient particles are not observed in the SEM image.

(2) Layer Including Flat Hair-Like Shape Crystalline Morphological Form

The flat hair-like shape crystalline morphological form to be described below occupies at least a part of the drug coating layer (including an amorphous form), equal to or greater than 50% by volume, equal to or greater than 80% by volume, (equal to or greater than 50% by volume as a crystal form, more and preferably equal to or greater than 70% by volume), and still more preferably nearly 100% by volume. In a case of occupying nearly 100% by volume, it is in a state that a plurality of crystalline morphological forms are not mixed, and only a single crystalline morphological form is present.

The layer including a flat hair-like shape crystalline morphological form is a drug coating layer in which crystals of a flatly elongated hair-like shape of crystals of the water-insoluble drug are randomly laminated on the substrate surface, and in which some of the crystals have a portion curved in shape, and crystals having other morphological forms are not mixed in the same crystal plane. In a case where an amorphous layer and a crystal layer are present, "not the same crystal plane" means that the amorphous film is present on the crystal layer. For example, the layer including the flat hair-like shape crystalline morphological form is a layer having the crystal form of Example 6 shown in FIG. 6A.

For example, characteristics of the layer including the flat hair-like shape crystalline morphological form are as follows.

1) A hair-like shape crystal having a long axis has a shape flatly jointed in a plurality of width directions, is not hollow, and has a tapered shape.

2) The joint shape of the hair-like shape crystal is randomly laminated on the substrate surface. The long axis is present in a state reclined along the substrate surface.

3) Some of the crystals have a portion curved in shape.

4) A length in the long-axis direction of the hair-like shape crystal is preferably 10 µm to 100 µm, more preferably about 20 µm, and is longer than a length of the crystalline morphological form of a long hollow object in many cases.

(3) Layer Including Morphological Form in which an Amorphous Film is Present on the Surface of the Flat Hair-Like Shape Crystal The layer is a drug coating layer in which the surface of the flat hair-like shape crystal is covered with an amorphous film. The layer including the morphological form in which an amorphous film is present on the surface of the flat hair-like shape crystal, in which a layer of an amorphous film is present on the flat hair-like shape crystal, is formed of two layers, one of the crystal and the other the amorphous film. For example, the layer including the morphological form in which an amorphous film is present on the surface of the flat hair-like shape crystal is a layer having the crystal form of Example 6 shown in FIG. 6B.

Specifically, on a certain plane (plane in which crystal/amorphous film are present), a certain crystal form is at least partly present, or a certain crystal form is present in an amount equal to or greater than 50% by volume, or equal to or greater than 80% by volume, (equal to or greater than 50% by volume as a crystal form, and more preferably equal to or greater than 70% by volume), still more preferably a plurality of crystal forms are not mixed, and an amorphous film may be present on the outside of a certain plane.

The crystal layers of the morphological form of the long hollow object, the morphological form of the flat hair-like shape, and the morphological form in which an amorphous film is present on the surface of the flat hair-like shape crystal have low toxicity and a high intravascular stenosis inhibitory effect when delivering medical equipment in which the substrate surface is coated with a drug into the body as a drug coating layer. While not limiting, it is considered that the reason is because solubility and retentivity in tissue after a drug having a certain crystal form is transferred into the tissue is affected. For example, in a case of an amorphous form, since solubility is high, even when the drug is transferred into a tissue, it immediately flows into the blood stream. Therefore, the retentivity in a tissue is low, and thus an excellent stenosis inhibitory effect cannot be obtained. On the other hand, the water-insoluble drug having the described specific crystal form effectively acts to inhibit the stenosis since when the drug is transferred into a tissue, one unit of the crystal becomes small, and therefore, the permeability into a tissue and the solubility thereof are excellent. In addition, it is considered that since the quantity of the drug remaining in a tissue as a large mass is small, the toxicity is low.

In particular, the layer including the crystalline morphological form of a long hollow object is a plurality of nearly uniform elongated bodies having long axes, and a morphological form which substantially uniformly stands in a row with regularity on the substrate surface. Therefore, the crystals transferred into a tissue have a small size (length in long-axis direction) of about 10 μm. For this reason, the drug uniformly acts on the lesion affected area, and tissue penetrability is increased. Further, it is considered that since the size of the crystals transferred is small, an excessive amount of the drug does not remain in the lesion affected area for an excessive amount of time, and the toxicity is not expressed, and a high stenosis inhibitory effect can be exhibited.

Water-Insoluble Drug

The water-insoluble drug means a drug that is insoluble or poorly soluble in water, and specifically, solubility in water is less than 5 mg/mL at pH 5 to 8. The solubility may be less than 1 mg/mL, and further, may be less than 0.1 mg/mL. The water-insoluble drug includes a fat-soluble drug.

Examples of some preferable water-insoluble drugs include immunosuppressive drugs such as cyclosporines including cyclosporine, immunoactive drugs such as rapamycin, anticancer drugs such as paclitaxel, an antiviral drug or an antibacterial drug, an antineoplastic tissue drug, an analgesic drug and an antiinflammatory drug, an antibiotic drug, an antiepileptic drug, an anxiolytic drug, an antiparalysis drug, an antagonist, a neuron blocking drug, an anticholinergic drug and a cholinergic drug, an antimuscarinic drug and a muscarinic drug, an antiadrenergic drug, an antiarrhythmic drug, an antihypertensive drug, a hormone drug, and a nutritional supplement.

The water-insoluble drug is preferably at least one selected from a group formed of rapamycin, paclitaxel, docetaxel, and everolimus. In the specification, rapamycin, paclitaxel, docetaxel, and everolimus include analogs and/or derivatives thereof as long as these have similar drug efficacy. For example, the paclitaxel is an analogue of the docetaxel. The rapamycin is an analogue of the everolimus. Among these, the paclitaxel is more preferable.

The water-insoluble drug may further include an excipient. The excipient is not limited as long as it is pharmaceutically acceptable, and examples thereof include water-soluble polymers, sugars, contrast agents, citric acid esters, amino acid esters, glycerol esters of short-chain monocarboxylic acid, pharmaceutically acceptable salts, surfactants, and the like.

Method for Preparing Crystalline Layer

A coating solution is prepared by dissolving a water-insoluble drug in a solvent. The coating solution is coated on a dilated balloon such that the solvent of the coating solution is slowly volatilized. Thereafter, the balloon is deflated after coating is dried, thereby preparing a drug coating layer including the crystal layer.

The solvent used is not particularly limited and is exemplified by tetrahydrofuran, ethanol, glycerin (also referred to as glycerol or propane-1,2,3-triol), acetone, methanol, dichloromethane, hexane, ethyl acetate, and water. Among these, a mixed solvent in which some from among tetrahydrofuran, ethanol, acetone, and water are mixed is preferable.

A coating solution is applied to the surface of a medical equipment (e.g. medical device, for example, balloon catheter, etc.) by using a coating apparatus. The coating apparatus includes a motor, a platform, and a dispensing tube. The motor is connected to a rotation member that is fixed to the proximal end of the medical equipment. The medical equipment is mounted on the rotation member and configured to rotate about its longitudinal axis. The medical equipment is supported on the platform so that the medical equipment is rotatable on the platform. The coating solution is coated on the surface of the medical equipment with the dispensing tube. The dispensing tube has a hollow tubular structure, and has an opening at the distal end. The lateral part of the distal portion of the dispensing tube is disposed to contact the surface of the medical equipment, and the coating solution is dispensed from the distal opening onto the surface of the medical equipment. The medical equipment is rotated about the longitudinal axis in the opposition direction (reverse direction) of dispensing the coating solution. The dispensing tube translates along the longitudinal axis of the medical equipment to apply the coating solution on the medical equipment. The coating solution applied on the surface of the medical equipment is dried to form a coating layer. The rotation of the medical equipment (balloon catheter) is made at 10-200 rpm, preferably 30-180 rpm, more preferably 50-150 rpm. The translational movement is made at 0.01-2 mm/sec, preferably 0.03-1.5 mm/sec, more preferably 0.05-1.0 mm/sec. The part of the medical equipment (balloon catheter) where a coating layer is formed has a round or annular shape in cross-section and its diameter is 1-10 mm, preferably 2-7 mm. The dispensing of the coating solution on the surface of the medical equipment is made at 0.01-1.5 μL/sec, preferably 0.01-1.0 μL/sec, more preferably 0.03-0.8 μL/sec.

Medical Equipment

The medical equipment can have the drug coating layer applied directly or through a pretreatment layer, such as a primer layer, on the surface of the substrate. The drug coating layer contains a drug at a density of 0.1 μg/mm$^2$ to 10 μg/mm$^2$, preferably at a density of 0.5 μg/mm$^2$ to 5 μg/mm$^2$, more preferably at a density of 0.5 μg/mm$^2$ to 3.5 μg/mm$^2$, even more preferably at a density of 1.0 μg/mm$^2$ to 3.0 μg/mm$^2$, but it is not particularly limited thereto.

The shape and materials of the substrate are not particularly limited. Metals and resins may be used as materials. The material may be any one of a film, a plate, a wire rod, and an irregularly shaped material, and may be a particulate.

The medical equipment used is not limited. Any medical equipment that is transplantable or insertable may be used. The medical equipment which is long, delivered in the non-dilated state with a reduced diameter in a body cavity such as blood, and enlarged in diameter in a circumferential direction at a part, such as a blood vessel or a tissue, to release a drug from the drug coating layer is preferable. Therefore, the medical equipment that is reduced in diameter to be delivered, and enlarged in diameter to be applied to an affected area is a medical equipment having a dilation portion. The drug coating layer is provided on at least a part of the surface of the dilation portion. That is, the drug is coated on, at least, the outer surface of the dilation portion.

The materials of the dilation portion of the medical equipment preferably have a certain degree of flexibility, and a certain degree of hardness such that the drug is released from the drug coating layer on the surface by being dilated when the medical equipment reaches a blood vessel or a tissue. Specifically, the medical equipment is constituted with a metal or a resin, and the surface of the dilation portion on which the drug coating layer is provided is preferably constituted of a resin. The resin constituting the surface of the dilation portion is not particularly limited, and preferable examples thereof include polyamides. That is, at least a part of the surface of the dilation portion of the medical equipment which is coated with a drug is a polyamide. Examples of the polyamide, which is not particularly limited as long as it is a polymer having an amide bond, include homopolymers such as polytetramethylene adipamide (Nylon 46), polycaprolactam (Nylon 6), polyhexamethylene adipamide (Nylon 66), polyhexamethylene sebacamide (Nylon 610), polyhexamethylene dodecamide (Nylon 612), polyundecanolactam (Nylon 11), polydodecanolactam (Nylon 12), copolymers such as a caprolactam/lauryl lactam copolymer (Nylon 6/12), a caprolactam/aminoundecanoic acid copolymer (Nylon 6/11), a caprolactam/w-aminononanoic acid copolymer (Nylon 6/9), a caprolactam/hexamethylene diammonium adipate copolymer (Nylon 6/66), and aromatic polyamides such as a copolymer of adipic acid and m-xylene diamine, or a copolymer of hexamethylene diamine and m,p-phthalic acid. Further, a polyamide elastomer which is a block copolymer in which Nylon 6, Nylon 66, Nylon 11, or Nylon 12 is a hard segment, and a polyalkylene glycol, a polyether, or an aliphatic polyester is a soft segment can be used as a substrate material for a medical device. The polyamides may be solely used, or two or more kinds thereof may be jointly used.

Specifically, as the medical equipment having the dilation portion, a long catheter having a dilation portion (stent) or a dilation portion (balloon) is exemplified.

In the balloon of one embodiment, preferably, the drug coating layer is formed on the surface at the time of dilating, and the balloon is wrapped (folded), inserted into a blood vessel, a body cavity or the like, delivered to tissue or affected area, and enlarged in diameter in the affected area, and then, the drug is released.

EXAMPLES

Hereinafter, examples and the comparative examples will be described, but, the embodiments are not limited to the examples.

Manufacture or Preparation of Drug Eluting Balloon, or Preparation of Non-Drug Coated Balloon Example 1

(1) Preparation of Coating Solution 1

L-serine ethyl ester hydrochloride (CAS No. 26348-61-8) (56 mg) and paclitaxel (CAS No. 33069-62-4) (134.4 mg) were weighed. Absolute ethanol (1.2 mL), tetrahydrofuran (1.6 mL), and RO (reverse osmosis) membrane-treated water (hereinafter, referred to as RO water) (0.4 mL) were respectively added thereto and dissolved, thereby preparing a coating solution 1.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 1 was coated on the dilated balloon such that the solvent of the coating solution is slowly volatilized to make the amount of paclitaxel be about 3 µg/mm². That is, a dispensing tube having an opening at the distal most end was transferred horizontally in the traverse direction and was placed on the surface of the balloon. At least a portion of the lateral side of the dispensing tube was contacted and disposed along the surface of the balloon. While at least a portion of the lateral side of the dispensing tube was maintained in contact with the surface of the balloon, the coating solution was dispensed from the opening at the distal most end of the dispensing tube. In this state the balloon was rotated about the longitudinal axis in the opposite direction (reverse direction) against the direction of the dispensing the coating solution from the distal opening. The translational movement of the dispensing tube along the longitudinal axis and the rotational movement of the balloon were adjusted, and concurrent with the beginning of the rotation, the coating solution was dispensed on the surface of the balloon at 0.053 µL/sec to perform coating of the balloon.

Thereafter, the coating was dried, thereby making a drug eluting balloon.

Example 2

(1) Preparation of Coating Solution 2

L-serine ethyl ester hydrochloride (70 mg) and paclitaxel (180 mg) were weighed. Absolute ethanol (1.5 mL), acetone (2.0 mL), tetrahydrofuran (0.5 mL), and RO water (1 mL) were added thereto respectively and dissolved, thereby preparing a coating solution 2.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 2 was coated on the dilated balloon such that the solvent of the coating solution is slowly volatilized to make the amount of paclitaxel be about 3 µg/mm².

That is, the coating was performed as in the Example 1 except that the coating solution was dispensed on the surface of the balloon at 0.088 µL/sec.

Thereafter, the coating was dried, thereby making a drug eluting balloon.

Example 3

(1) Preparation of Coating Solution 3

L-serine ethyl ester hydrochloride (70 mg) and paclitaxel (168 mg) were weighed. Absolute ethanol (1.5 mL), tetrahydrofuran (1.5 mL), and RO water (1 mL) were added thereto respectively and dissolved, thereby preparing a coating solution 3.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 3 was coated on the dilated balloon such that the solvent of the coating solution is slowly volatilized to make the amount of paclitaxel be about 3 µg/mm².

That is, the coating was performed as in the Example 1 except that the coating solution was dispensed on the surface of the balloon at 0.101 µL/sec.

Thereafter, the coating was dried, thereby making a drug eluting balloon.

Example 4

(1) Preparation of Coating Solution 4

L-serine ethyl ester hydrochloride (70 mg) and paclitaxel (180 mg) were weighed. Absolute ethanol (1.75 mL), tetrahydrofuran (1.5 mL), and RO water (0.75 mL) were added thereto respectively and dissolved, thereby preparing a coating solution 4.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 4 was coated on the dilated balloon such that the solvent of the coating solution is slowly volatilized to make the amount of paclitaxel be about 3 µg/mm$^2$.

That is, the coating was performed as in the Example 1 except that the coating solution was dispensed on the surface of the balloon at 0.092 µL/sec.

Thereafter, the coating was dried, thereby making a drug eluting balloon.

Example 5

(1) Preparation of Coating Solution 5

L-aspartic acid dimethyl ester hydrochloride (CAS No. 32213-95-9) (37.8 mg) and paclitaxel (81 mg) were weighed. Absolute ethanol (0.75 mL), tetrahydrofuran (0.96 mL), and RO water (0.27 mL) were added thereto respectively and dissolved, thereby preparing a coating solution 5.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 5 was coated on the dilated balloon such that the solvent of the coating solution is slowly volatilized to make the amount of paclitaxel be about 3 µg/mm$^2$.

That is, the coating was performed as in the Example 1 except that the coating solution was dispensed on the surface of the balloon at 0.055 µL/sec.

Thereafter, the coating was dried, thereby making a drug eluting balloon.

Example 6

(1) Preparation of Coating Solution 6

L-serine ethyl ester hydrochloride (56 mg) and paclitaxel (134.4 mg) were weighed. Absolute ethanol (0.4 mL), tetrahydrofuran (2.4 mL), and RO water (0.4 mL) were added thereto respectively and dissolved, thereby preparing a coating solution 6.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 6 was coated on the dilated balloon such that the solvent of the coating solution is slowly volatilized to make the amount of paclitaxel be about 3 µg/mm$^2$.

That is, the coating was performed as in the Example 1 except that the coating solution was dispensed on the surface of the balloon at 0.053 µL/sec.

Thereafter, the coating was dried, thereby making a drug eluting balloon.

Comparative Example 1

IN.PACT (manufactured by INVAtec JAPAN) which is a commercially available balloon catheter was prepared. The balloon in Comparative example 1 is a drug eluting balloon of which the surface is coated with paclitaxel.

Comparative Example 2

A balloon catheter (manufactured by Terumo Corp., the material of the balloon (dilation portion) is a nylon elastomer) having a size of a diameter 3.0×a length 20 mm (dilation portion) when dilated was prepared. The balloon in Comparative example 2 is a non-drug coated balloon of which the surface is not coated with a drug.

Measurement of Amount of Paclitaxel Coated on Balloon

For the drug eluting balloon in Examples 1 to 6, the amount of paclitaxel coated on the balloon was measured according to the following procedure.

1. Method

After the prepared drug eluting balloon was immersed in a methanol solution, it was shaken with a shaking apparatus for 10 minutes, and then, paclitaxel coated on the balloon was extracted. The absorbance at 227 nm of the methanol solution by which paclitaxel was extracted was measured by high performance liquid chromatography using an ultraviolet-visible spectrophotometer, and the amount of paclitaxel per balloon ([µg/balloon]) was determined. In addition, the amount of paclitaxel per unit area of balloon ([µg/mm$^2$]) was calculated from the amount of obtained paclitaxel and the balloon surface area.

2. Result

Table 1 shows the obtained results. In addition, in Table 1, "Balloon surface area" represents a surface area (unit: mm$^2$) when the balloon is dilated, "per each balloon" in "Amount of PTX on a balloon" represents the amount of paclitaxel per one balloon (unit: µg/balloon), and "per unit area" in "Amount of PTX on a balloon" represents the amount of paclitaxel per surface area 1 mm$^2$ of the balloon (unit: µg/mm$^2$), respectively.

As shown in Table 1, the amount of paclitaxel coated on the balloon in all of Examples 1 to 6 is about 3 µg/mm$^2$, and it was possible to coat the target amount of paclitaxel on the balloon surface.

TABLE 1

| Examples/ Comparative examples | Coating solution No. | Amount of PTX on a balloon | |
|---|---|---|---|
| | | per each [µg/balloon] | per unit area [µg/mm$^2$] |
| 1 | Coating solution 1 | 588.9 | 3.1 |
| 2 | Coating solution 2 | 665.5 | 3.5 |
| 3 | Coating solution 3 | 652.6 | 3.5 |
| 4 | Coating solution 4 | 661.3 | 3.5 |
| 5 | Coating solution 5 | 653.3 | 3.5 |
| 6 | Coating solution 6 | 560.2 | 3.0 |

Observation of Drug Coating Layer of Drug Eluting Balloon by Scanning Electron Microscope (SEM)

1. Method

The drug eluting balloons in Examples 1 to 5 (FIGS. 1 to 5) and Example 6 (FIG. 6) were dried, and after the dried drug eluting balloons were cut to an appropriate size, these were placed on a support, and platinum deposition was performed thereon. In addition, in the same manner, after a commercially available drug eluting balloon (IN.PACT) manufactured by INVAtec JAPAN in Comparative example 1 also was cut to an appropriate size, it was placed on a support, and platinum deposition was performed thereon.

The surface and the inside of the drug coating layers of these platinum deposited samples were observed by a scanning electron microscope (SEM).

2. Result

In the drug coating layers of the Examples, crystal layers having a morphological form of a long hollow object, a morphological form of a flat hair-like shape, and a morphological form in which an amorphous film is present on the surface of the flat hair-like shape crystals were observed.

SEM images shown in FIGS. 1 to 6 were obtained. FIGS. 1 to 5, which are SEM images of Examples 1 to 5, show a layer, including the morphological form of a long hollow object, and it was made clear that uniform paclitaxel crystals of the long hollow objects having a length of about 10 μm are uniformly formed on the balloon surface. These paclitaxel crystals of the long hollow objects have long axes, and the elongated bodies (about 10 μm) having the long axes were formed so as to be in a direction nearly perpendicular to the balloon surface. The diameter of an elongated body was about 2 μm. In addition, the cross section of the elongated body in a surface perpendicular to the long axis was a polygon. The polygon was, for example, a polygon of a tetragon. Further, these nearly uniform long hollow objects of paclitaxel were uniformly and densely (at the same density) formed on the entire surface of the balloon in the same morphological form (structure and shape).

Figure 6A:
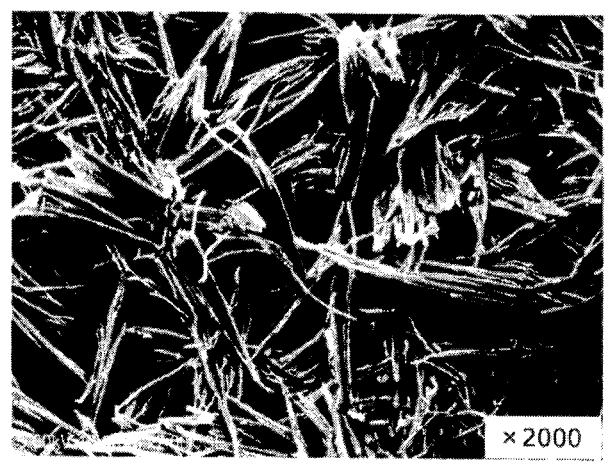
FIG. 6A is a diagram showing a SEM image at 2,000 times magnification of crystals observed on the substrate surface of the drug coating layer prepared in Example 6.
Figure 6B:
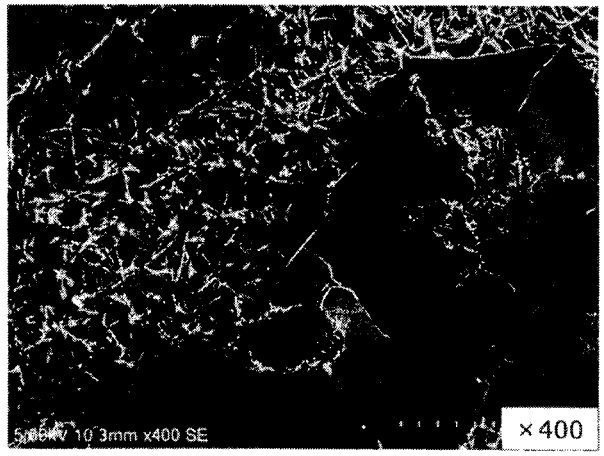
FIG. 6B is a diagram showing a SEM image at 400 times magnification of crystals observed on another portion of the substrate surface of the drug coating layer prepared in Example 6.

On the other hand, SEM images of FIG. 6A and FIG. 6B in Example 6 show a layer including a morphological form of a flat hair-like shape and a morphological form in which an amorphous film is present on the surface of the flat hair-like shape crystals, which were paclitaxel crystals of a flatly elongated hair-like shape. Many of these crystals have a comparatively large size equal to or greater than 20 μm, and the long axes are present in a state reclined along the balloon surface (FIG. 6A). Further, as shown in FIG. 6B, a region in which the upper portion of a layer including a morphological form of a flat hair-like shape is covered with an amorphous film was present. In the region, the layer including a morphological form in which a layer of an amorphous film is present on the flat crystal structure, two layers are formed of the crystals and the amorphous film, and the amorphous film is present on the surface of the flat hair-like shape crystals.

Figure 7:
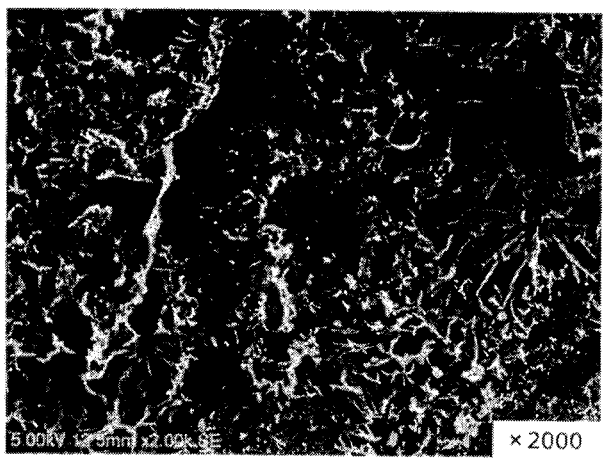
FIG. 7 is a diagram showing a SEM image at 2,000 times magnification of crystals observed on the substrate surface of the drug coating layer of a commercially available drug eluting balloon (IN.PACT) manufactured by INVAtec JAPAN in Comparative example 1.

FIG. 7 in Comparative example 1 is a SEM image of the drug coating layer of a commercially available drug eluting balloon (IN.PACT) manufactured by INVAtec JAPAN. In this, amorphous material and crystals were mixed in the same plane. It was observed that most of them were nearly amorphous, and needle-like crystals were partly mixed in the same plane.

Intravascular Stenosis Inhibitory Effect in a Pig Coronary Artery and Effect on Blood Vessel Remodeling For Examples 1 and 6, Comparative example 1 (C1: commercially available balloon), and Comparative example 2 (C2: non-drug coated balloon), the intravascular stenosis inhibitory effect in a pig coronary artery and an effect on blood vessel remodeling were evaluated in accordance with the following procedure.

1. Method (1) A guiding catheter with a guide wire was inserted by an 8 Fr sheath, and guided to the left and right coronary artery opening portion under X-ray fluoroscopy.

(2) Angiography of each coronary artery was performed (coronary artery: left anterior descending coronary artery (LAD), right coronary artery (RCA), and left circumflex coronary artery (LCX)), and a diameter of coronary artery obtained by angiography was measured by a QCA software.

(3) A site in which a diameter of a stent is 1.2 times, and a diameter of the drug eluting balloon is 1.3 times with respect to a diameter of a blood vessel was selected, and work after stent placement was performed.

(4) After extended for 30 seconds such that BMS (bare metal stent) stent (stent diameter 3 mm×length 15 mm) in the coronary artery selected is 1.2 times, a balloon catheter for the stent placement was removed. At the stent placement site, after the drug eluting balloon (balloon diameter 3 mm×length 20 mm) having the drug coating layer prepared in Examples 1 and 6 and Comparative examples 1 and 2 was dilated for 1 minute so as to be 1.3 times with respect to the diameter of a blood vessel, the balloon catheter was removed.

(5) After the drug eluting balloon was dilated, the guiding catheter and the sheath were removed. After a central side of a carotid artery was ligated, a gap of exfoliated muscles of an incision opening of cervical region was sutured with a suture, and the skin was sutured by a surgical stapler for sutures.

(4) 28 days after the balloon dilatation, autopsy was performed.

Calculation Method of Intravascular Stenosis Rate

An intravascular stenosis rate was calculated in accordance with the following procedure.

Blood vessel images were taken by a Leica microscope and a pathology imaging system. By these images, internal area of an external elastic lamina area, internal elastic lamina area, internal area of lumen, internal area of stent were measured.

Area stenosis rate (%) was calculated from "area stenosis rate=(neointimal area/internal elastic lamina area)×100".

Calculation Method of a Fibrin Content, Fibrin Content Score

Evaluation of fibrin content was performed in all circumferences of blood vessel according to the method of Suzuki et al. (Suzuki Y., et. al Stent-based delivery of sirolimus reduces neointimal formation in aprocine coronary model. Circulation 2001; 1188-93).

The content of the score of fibrin content is as follows.

Score 1: Fibrin localized in a blood vessel was observed, or fibrin is moderately deposited in a region less than 25% of all circumferences of blood vessel observable near a strut of the stent.

Score 2: Fibrin is moderately deposited in a region greater than 25% of all circumferences of blood vessel observable, or fibrin is heavily deposited in a region less than 25% of all circumferences of blood vessel observable between the struts and the proximity of the strut.

Score 3: Fibrin is severely deposited in a region greater than 25% of all circumferences of blood vessel observable.

In addition, all the scores were obtained by calculating the average value of the three locations, that is, a proximal location, a middle location, and a distal location of the stent placement sites for each blood vessel.

Endothelialization Score Calculation Method, Endothelialization Score

The content of an endothelialization score is as follows.

Score 1: Up to 25% of all circumferences of vascular lumen observable is covered with endothelial cells.

Score 2: 25% to 75% of all circumferences of vascular lumen observable is covered with endothelial cells.

Score 3: Equal to or greater than 75% of all circumferences of vascular lumen observable is covered with endothelial cells.

In addition, all the scores were calculated as an average value of three locations, that is, a proximal, a middle and a distal location to the stent placement site, for each blood vessel.

2. Results for Intravascular Stenosis Inhibitory Effect in a Pig Coronary Artery An intravascular stenosis rate was calculated according to the above-described procedure. Table 2 shows the obtained results. In Table 2, 1 and 6 in a column of Examples/Comparative examples are Examples, and C1 to C2 are Comparative examples.

Figure 8:
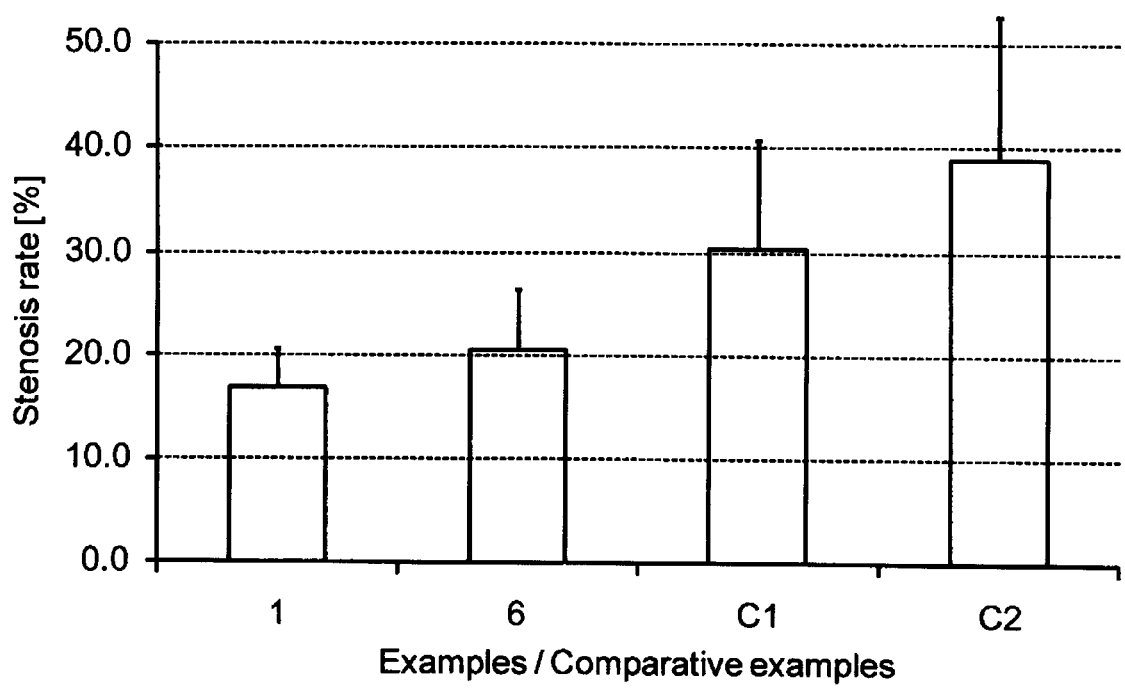
FIG. 8 is a graph of an intravascular stenosis rate (%) showing an inhibitory effect on an intravascular stenosis in a pig coronary artery.

In addition, FIG. 8 is a graph showing the blood vessel stenosis rate of Examples 1 and 6, and of Comparative examples C1 to C2 for the intravascular stenosis inhibitory effect in pig coronary arteries. In FIG. 8, the horizontal axis represents Examples or Comparative Examples, the numbers 1 and 6 mean Examples 1 and 6, respectively, and the numbers with letters, that is, C1 to C2 mean Comparative example 1 (C1) and Comparative example 2 (C2), respectively. In addition, the vertical axis represents the area stenosis rate (unit: %) of a blood vessel.

In Comparative Example 2 (C2), the area stenosis rate of a blood vessel treated with the non-drug coated balloon as a non-drug treated control was 38.9%. The area stenosis rate of a blood vessel treated with the drug eluting balloon in Example 6 was 20.6%, and a significant stenosis inhibitory effect was confirmed as compared to the non-drug treated control. On the other hand, the area stenosis rate of a blood vessel treated with the commercially available drug eluting balloon (IN.PACT) in Comparative example 1 was 30.4%, and it was found that the area stenosis rate tends to be decreased as compared to the non-drug coated balloon; however, it was estimated that there is sufficient room for improvement in the effect.

In contrast, the area stenosis rate of a blood vessel treated with the drug eluting balloon according to Example 1 was 16.8%, and a significant stenosis inhibitory effect was observed as compared to the non-drug treated control and the IN.PACT of Comparative example 1 (C1). In addition, it showed a stronger effect than in Example 6, and the most excellent stenosis inhibitory effect was obtained.

Based on what has been described above, it was made clear that the drug eluting balloon of the drug coating layer having the paclitaxel crystalline morphological form according to Examples 1 and 6 exhibits a significantly stronger stenosis inhibitory effect than the commercially available drug eluting balloon.

TABLE 2

| Examples/Comparative examples | Stenosis rate [%] | S.D. |
| --- | --- | --- |
| 1 | 16.8 | 3.9 |
| 6 | 20.6 | 5.9 |
| C1 | 30.4 | 10.3 |
| C2 | 38.9 | 13.8 |

3. Results for Blood Vessel Remodeling after Stent Placement in a Pig Coronary Artery (Toxicity)

As the effect (toxicity) on the blood vessel remodeling after the stent placement in a pig coronary artery, the fibrin content score and endothelialization score were observed. The results are shown in Table 3. Moreover, the larger the number the fibrin content score is, the larger the fibrin content is, which is not preferable. On the other hand, the smaller the number the endothelialization score is, the less blood vessel is covered with the endothelial cells, which is not preferable. In Table 3, 1 and 6 in a column of Examples/Comparative examples are Examples, and C1 and C2 are Comparative examples.

The fibrin content score and endothelialization score of a blood vessel treated with the non-drug coated balloon as a non-drug treated control in Comparative example 2 (C2) do not have an influence on the vascular remodeling since there is no effect (toxicity) by drugs, and the scores were 1.00±0.00 and 3.00±0.00, respectively.

The fibrin content score and endothelialization score in Comparative example 1 (C1) were 1.27±0.15 and 2.80±0.11, respectively, and the scores were nearly the same as those in the non-drug coated balloon. It is estimated that effect (toxicity) on the vascular remodeling is also small since the stenosis inhibition effect by drugs is small.

On the other hand, the fibrin content score and endothelialization score of a blood vessel treated with the drug eluting balloon according to Example 6 were 2.61±0.16 and 1.78±0.17, respectively, and it was suggested that the effect on the vascular remodeling was great as compared to those of Comparative example 1 (C1) and Comparative example 2 (C2). It is considered that this is because the stenosis inhibition effect is stronger than in Comparative example 1 (C1) and Comparative example 2 (C2).

In contrast, the fibrin content score and endothelialization score of a blood vessel treated with the drug eluting balloon according to Example 1 were 1.53±0.17 and 2.87±0.09, respectively, and it was made clear that the effect (toxicity) on the vascular remodeling was the same as that of the commercially available product in Comparative example 1 (C1), and in spite that high stenosis inhibition effect was obtained, the toxicity was extremely low.

Based on what has been described above, the drug eluting balloon of the drug coating layer having the paclitaxel crystalline morphological form according to Example 6 has a significantly stronger stenosis inhibition effect. Further, it was made clear that the drug eluting balloon of the drug coating layer having the paclitaxel crystalline morphological form according to Example 1 has a significantly stronger stenosis inhibition effect, hardly exhibits the effect (toxicity) on the vascular remodeling, and thus, it is an excellent drug eluting balloon in terms of effectiveness and side effects (toxicity).

TABLE 3

| Examples/Comparative examples | Fibrin content score | Endothelialization score |
| --- | --- | --- |
| 1 | 1.53 ± 0.17 | 2.87 ± 0.09 |
| 6 | 2.61 ± 0.16 | 1.78 ± 0.17 |
| C1 | 1.27 ± 0.15 | 2.80 ± 0.11 |
| C2 | 1.00 ± 0.00 | 3.00 ± 0.00 |

The detailed description above describes a drug coating layer disclosed by way of example. The invention is not limited, however, to the precise embodiment and variations described. Various changes, modifications and equivalents can be employed by one skilled in the art without departing from the spirit and scope of the invention as defined in the accompanying claims. It is expressly intended that all such changes, modifications and equivalents which fall within the scope of the claims are embraced by the claims.

What is claimed is:

1. A drug coating layer on a non-porous nylon elastomer balloon substrate surface comprising a plurality of elongated bodies with long axes wherein each elongated body is formed of a crystal of a water-insoluble drug and is independently formed on the substrate surface,
  wherein the long axes of the elongated bodies are substantially linear in shape, a cross-sectional shape of the elongated body on a surface perpendicular to the long axis is a polygon, and the long axes of the elongated bodies form an angle in a predetermined range with respect to a substrate plane with which the long axis of the elongated body intersects.

2. The drug coating layer according to claim 1, wherein the elongated body is hollow.

3. The drug coating layer according to claim 1, wherein the water-insoluble drug is rapamycin, paclitaxel, docetaxel, or everolimus.

4. A method for delivering a drug, comprising:
  delivering a nylon elastomer balloon with the drug coating layer on the balloon substrate surface according to claim 1 to a lumen;
  radially dilating the nylon elastomer balloon; and
  applying the drug coating layer to the lumen.

\* \* \* \* \*